(12) United States Patent
Yahata et al.

(10) Patent No.: US 8,561,388 B2
(45) Date of Patent: Oct. 22, 2013

(54) FAILURE DETECTION APPARATUS FOR PARTICULATE FILTER

(75) Inventors: Shigeto Yahata, Obu (JP); Tomohiro Ueno, Nagoya (JP)

(73) Assignee: Denso Corporation, Kariya (JP)

( * ) Notice: Subject to any disclaimer, the term of this patent is extended or adjusted under 35 U.S.C. 154(b) by 181 days.

(21) Appl. No.: 13/313,235

(22) Filed: Dec. 7, 2011

(65) Prior Publication Data

US 2012/0144813 A1 Jun. 14, 2012

(30) Foreign Application Priority Data

Dec. 8, 2010 (JP) ................................ 2010-273591

(51) Int. Cl.
*F01N 3/00* (2006.01)

(52) U.S. Cl.
USPC ................ 60/277; 60/274; 60/297; 60/311

(58) Field of Classification Search
USPC ................................................. 60/274–324
See application file for complete search history.

(56) References Cited

U.S. PATENT DOCUMENTS

| | | | | |
|---|---|---|---|---|
| 4,656,832 A * | 4/1987 | Yukihisa et al. | ................. | 60/303 |
| 6,432,168 B2 * | 8/2002 | Schonauer | ......................... | 95/18 |
| 7,628,007 B2 * | 12/2009 | Kittelson et al. | ................. | 60/277 |
| 8,310,249 B2 * | 11/2012 | Paterson | ........................ | 324/693 |
| 2008/0282682 A1 * | 11/2008 | C. et al. | ............................ | 60/291 |
| 2009/0301062 A1 * | 12/2009 | Sumida et al. | ................... | 60/285 |
| 2012/0117945 A1 * | 5/2012 | Krafthefer et al. | ............... | 60/274 |

FOREIGN PATENT DOCUMENTS

| | | |
|---|---|---|
| JP | S62-035252 | 2/1987 |
| JP | 2006-307701 | 11/2006 |
| JP | P2009-144577 A | 7/2009 |

* cited by examiner

*Primary Examiner* — Kenneth Bomberg
*Assistant Examiner* — Jesse Bogue
(74) *Attorney, Agent, or Firm* — Nixon & Vanderhye PC

(57) ABSTRACT

A detection apparatus is used to detect a failure of a particulate filter. The detection apparatus includes a PM (particulate matter) sensor, a timing estimating unit, and a failure determining unit. The PM sensor is disposed at a downstream side of the particulate filter in an exhaust passage. The PM sensor includes a pair of electrodes and detects an amount of the PM based on current passing through the PM deposited between the electrodes. The estimating unit estimates a failure-state energization timing at which the PM sensor starts to be energized due to the PM deposited between the electrodes assuming that the particulate filter has failed. The determining unit determines that the particulate filter is in a failure state when an actual energization timing of the PM sensor based on an output of the PM sensor is earlier than the failure-state energization timing estimated.

15 Claims, 10 Drawing Sheets

FIG.1
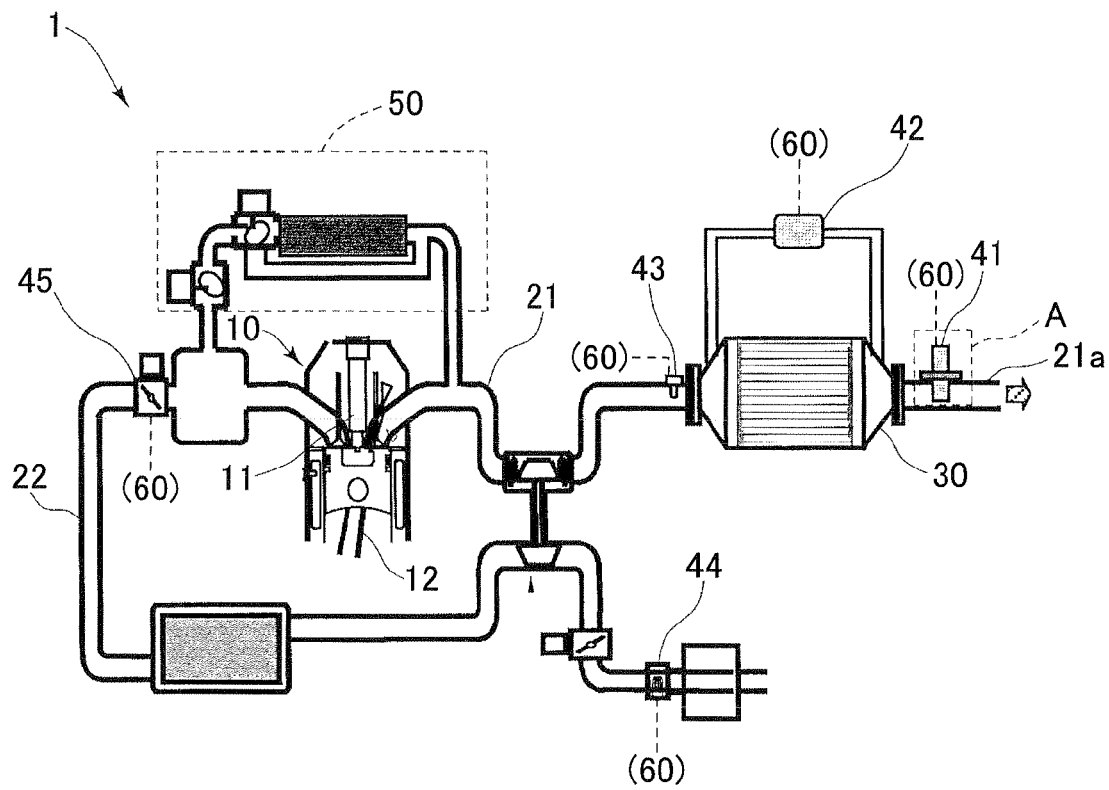
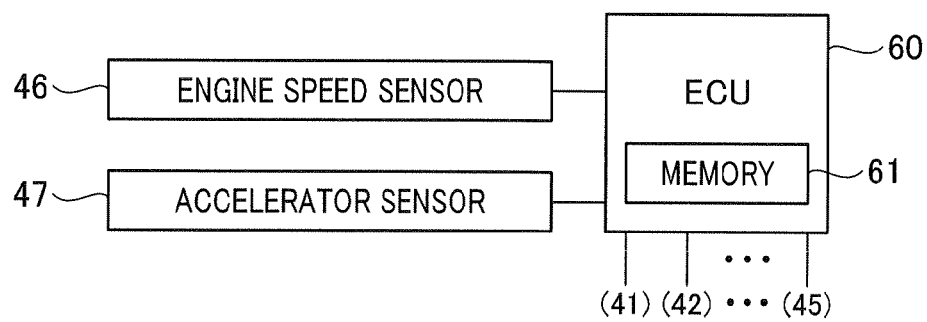

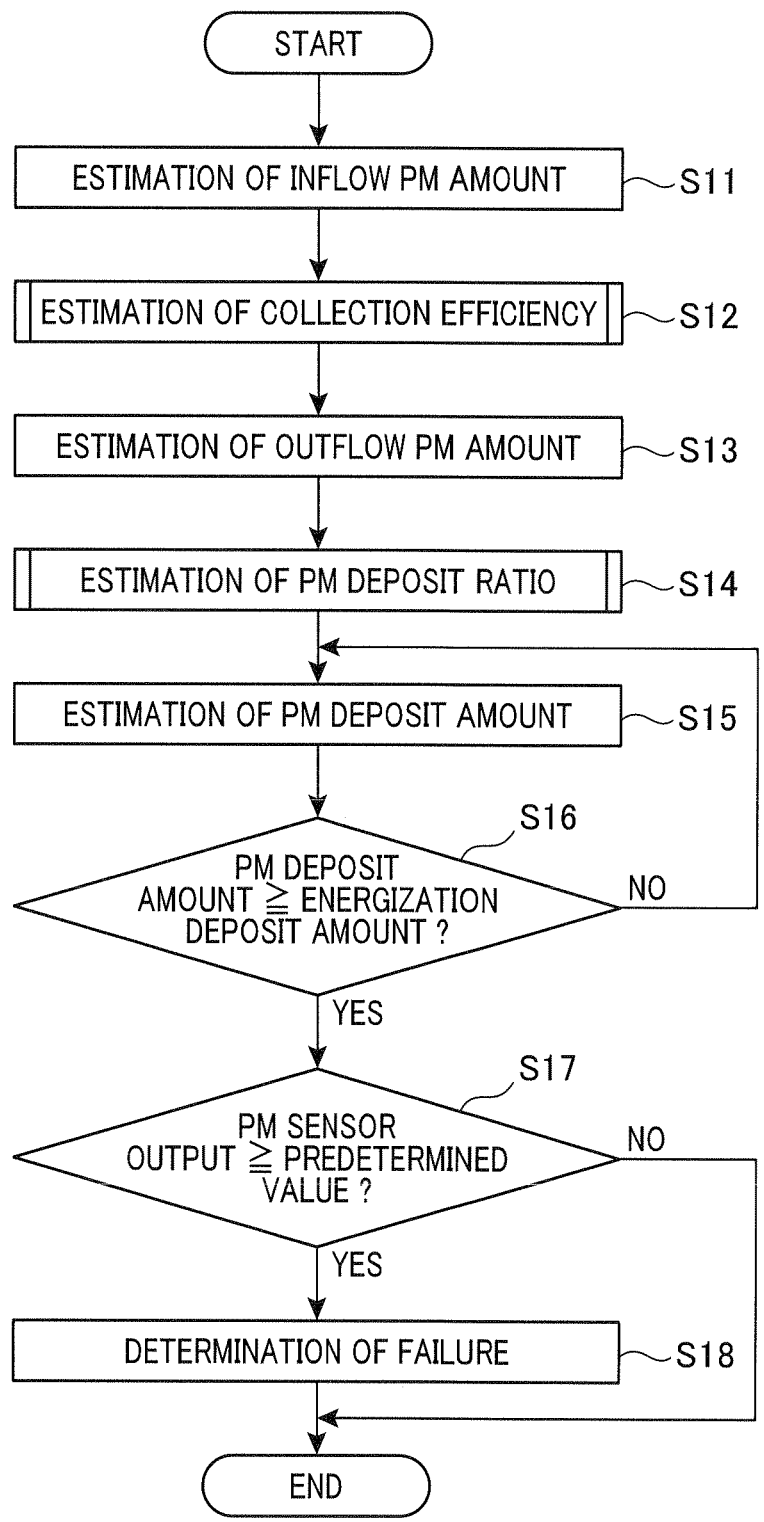

START → CALCULATION OF PM ACCUMULATION AMOUNT (S121) → CALCULATION OF EXHAUST FLOW RATE (S122) → CALCULATION OF COLLECTION EFFICIENCY (S123) → RETURN

START → ESTIMATION OF ELECTRODE TEMPERATURE (S141) → CALCULATION OF PM DEPOSIT RATIO (S142) → RETURN

PASSAGE OF TIME FROM COMPLETION OF HEATER REGENERATION

EXHAUST FLOW RATE

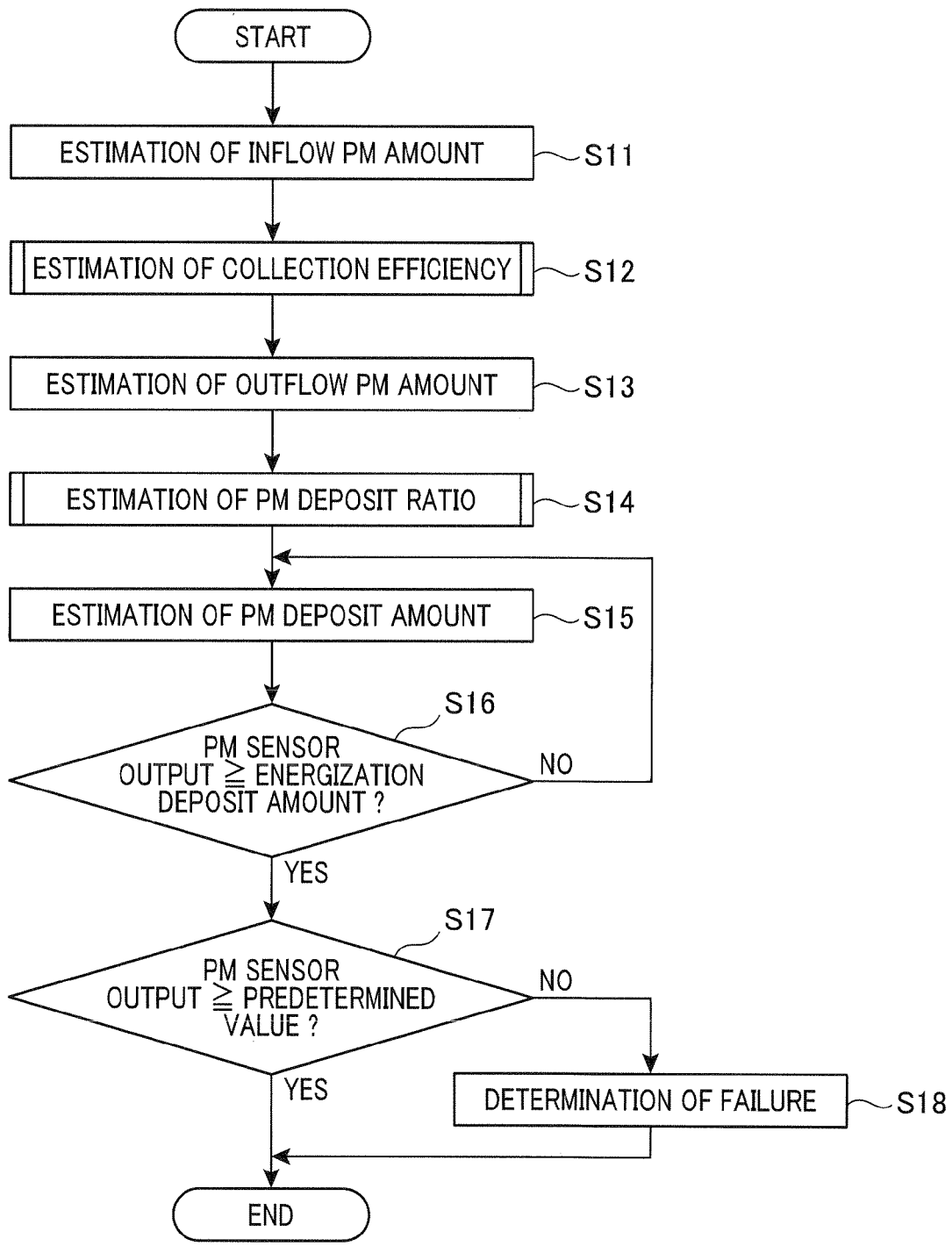

FAILURE DETECTION APPARATUS FOR PARTICULATE FILTER

CROSS-REFERENCE TO RELATED APPLICATION

This application is based on and claims the benefit of priority from earlier Japanese Patent Application No. 2010-273591 filed Dec. 8, 2010, the description of which is incorporated herein by reference.

BACKGROUND OF THE INVENTION

1. Technical Field of the Invention

The present invention relates to a failure detection apparatus for detecting a failure of a particulate filter that collects particulate matter contained in the exhaust gas of an internal combustion engine.

2. Related Art

In order to reduce soot discharged from an combustion engine such as a diesel engine in the related art, a diesel particulate filter (DPF), which collects granular matter, i.e., so-called particulate matter (PM) constituting the soot, can be disposed in an exhaust passage of the engine. Such a DPF is ensured to be repeatedly usable by periodically performing regeneration process in which the PM accumulated in the DPF are burned and removed.

However, the regeneration process may cause the temperature of the DPF to be excessively elevated. In this case, the DPF may be melted or broken due to the excessively elevated temperature (the DPF may fail). When the DPF is in a failure state, the PM that passes through the DPF is increased, and thus the DPF is unlikely to satisfy the emission limits.

Recently, development of a failure detection apparatus that detects a failure of the DPF is desired, because of request of On-Board Diagnostics (OBD) performed by a computer mounted on a vehicle. As such an apparatus, a failure detection apparatus using an electrode-type PM sensor (see JP-A-2009-144577 and JP-A-S62-035252) that detects an amount of PM is suggested (see JP-A-2009-144577).

An electrode-type PM sensor is configured by providing a pair of electrodes on an insulating base. The PM sensor is located in an exhaust path, and upon a use of the PM sensor, a voltage is applied across the pair of electrodes.

The PM contained in an exhaust gas is deposited on the electrical insulating material between the pair of electrodes. The PM is composed of carbon particles and has electrical conductivity. Accordingly, increase in the amount of deposited PM allows current to pass across the pair of electrodes (i.e. the PM sensor is energized). The value of the current is equivalent to the amount of deposited PM, i.e. equivalent to the amount of PM contained in the exhaust gas. The PM sensor reads the value of current (resistance between the electrodes, which is equivalent to the value of current) to thereby detect the amount of PM.

If the DPF is in a failure state, the amount of PM passing through the DPF will be increased and the resistance across the pair of electrodes of the PM sensor will be decreased. For this, the failure detection apparatus disclosed in JP-A-2009-144577 is configured to detect the resistance of the PM sensor (output of the PM sensor). In this device, when the resistance becomes smaller than a reference resistance, a failure is determined as having occurred in the DPF. In other words, the failure detection apparatus disclosed in JP-A-2009-144577 detects a failure of the DPF based on the absolute value of the output from the PM sensor.

However, the PM that has been deposited on the insulating material between the electrodes of the PM sensor will have an electrical resistance which considerably varies depending on temperature. Specifically, the failure detection apparatus disclosed in JP-A-2009-144577, for example, may determine the DPF as being in a failure state irrespective of the DPF's being in a normal state, or determine the DPF as being in a normal state irrespective of the DPF's being in a failure state. Thus, the failure of the DPF is not accurately detected with such a failure detection apparatus as disclosed in JP-A-2009-144577.

SUMMARY OF THE INVENTION

The present invention has been made in light of the conditions set forth above and has as its object to provide a failure detection apparatus for a particulate filter, which is able to detect a failure of a particulate filter with good accuracy.

According to an exemplary aspect of the present invention, there is provided a failure detection apparatus for detecting a failure of a particulate filter that is disposed in an exhaust passage of an internal combustion engine and collects particulate matter (PM) contained in exhaust gas of the internal combustion engine, comprising: a PM sensor that is disposed at a downstream side of the particulate filter in the exhaust passage, which includes a pair of electrodes between which the PM is deposited to allow current to flow between the pair of electrodes, and detects an amount of the PM based on current passing through the PM deposited between the pair of electrodes; a timing estimating unit that estimates a failure-state energization timing that is an upper limit of the energization timing at which the PM sensor starts to be energized due to the PM deposited between the pair of electrodes assuming that the particulate filter has failed; and a failure determining unit that determines that the particulate filter is in a failure state when an actual energization timing of the PM sensor based on an output of the PM sensor is earlier than the failure-state energization timing estimated by the timing estimating unit.

Thus, the timing estimating unit estimates a maximum energization timing (failure-state energization timing) of the PM sensor that would occur if the particulate filter in a failure state. The energization timing of the PM sensor depends on the amount of PM deposited between the electrodes, but will not depend on the temperature variation of the PM deposited between the electrodes (electrical resistance variation of the PM). When the particulate filter is in a failure state, the amount of PM passing through the particulate filter is increased. Accordingly, the PM sensor in a failure state becomes energized earlier than that in a normal state. Thus, the failure determining unit determines the particulate filter to be in a failure state when the actual energization timing is earlier than the failure-state energization timing estimated by the timing estimating unit. Therefore, the failure of the particulate filter can be detected with good accuracy, irrespective of the temperature variation of the PM deposited between the electrodes.

In the exemplary aspect, the PM sensor may include a heater that heats the PM sensor to burn and remove the PM deposited between the pair of electrodes. The timing estimating unit may estimate the failure-state energization timing after a burning and removal of the PM due to the heater.

Thus, since the PM sensor includes the heater for burning and removing the PM, the PM is burned and removed by the heater so that the PM sensor is continuously usable. In this case, the timing estimating unit estimates the failure-state energization timing after burning and removing the PM, i.e.

the failure-state energization timing from when the PM is burned and removed and no PM is deposited between the electrodes. Accordingly, the estimated value as obtained of failure-state conduction timing will have high accuracy.

In the exemplary aspect, the timing estimating unit may includes: an inflow PM amount estimating unit that estimates an inflow PM amount that is an amount of the PM flowing into the particulate filter; a collection efficiency estimating unit that estimates a failure-state collection efficiency that is a collection efficiency of the particulate filter when the particulate filter has failed; an outflow PM amount estimating unit that estimates a failure-state outflow PM amount that is an amount of the PM flowing out of the particulate filter when the particulate filter is in a failure state based on the inflow PM amount estimated by the inflow PM amount estimating unit and the failure-state collection efficiency estimated by the collection efficiency estimating unit. The timing estimating unit may estimate the failure-state energization timing based on the failure-state outflow PM amount estimated by the outflow PM amount estimating unit.

In this regard, when the particulate filter is in a failure state, the collection efficiency of PM is lowered compared to a normal state and thereby increases the outflow PM amount of the particulate filter. Thus, the collection efficiency estimating unit estimates a failure-state collection efficiency of the particulate filter in a failure state, while the outflow PM amount estimating unit estimates a failure-state outflow PM amount based on the outflow PM amount and the failure-state collection efficiency. In this way, the estimated value as obtained of the failure-state outflow PM amount will have high accuracy.

Meanwhile, the energization timing of the PM sensor depends on the failure-state outflow PM amount. Thus, the timing estimating unit estimates a failure-state energization timing based on the failure-state outflow PM amount. In this way, the estimated value as obtained of the failure-state energization timing will have high accuracy.

In the exemplary aspect, the timing estimating unit may include: a deposit ratio estimating unit that estimates a PM deposit ratio that is a ratio of the PM deposited on the pair of electrodes with respect to all of the PM included in exhaust gas at a downstream side of the particulate filter in the exhaust passage; a deposit amount calculating unit that calculates an integrated value of a failure-state PM deposit amount by integrating it with time, the failure-state PM deposit amount being an amount of the PM deposited between the pair of electrodes assuming that the particulate filter has failed, and the timing estimating unit that estimates, as the failure-state energization timing, an timing at which the integrated value of the failure-state PM deposit amount becomes not less than a energization deposit amount that is predetermined as PM deposit amount at the energization timing.

In this regard, the energization timing is influenced by the integrated value of the PM deposited between the electrodes. Thus, the deposit amount calculating unit calculates a failure-state PM deposit amount by integrating PM deposit amount with time. Then, the timing estimating unit estimates the timing when the failure-state PM deposit amount becomes equal to or more than the energization deposit amount, i.e. estimates a failure-state energization timing. In this way, the estimated value as obtained of the failure-state energization timing will have high accuracy.

In this case, the PM deposit amount depends on PM deposit ratio. Therefore, the deposit ratio estimating unit estimates a PM deposit ratio. Then, the deposition calculating unit calculates a failure-state PM deposit amount based on the PM deposit ratio and the failure-state outflow PM amount. In this way, the estimated value as obtained of the failure-state PM deposit amount will have high accuracy.

In the exemplary aspect, the collection efficiency estimating unit may include an accumulation amount calculation unit that calculates a PM accumulation amount that is an amount of the PM accumulated on the particulate filter, and estimates the failure-state collection efficiency based on the PM accumulation amount by the accumulation calculation unit.

In this regard, the inventors of the present invention have expertise that collection efficiency depends on PM accumulation amount. Thus, the collection efficiency estimating unit estimates a failure-state collection efficiency based on a PM accumulation amount. In this way, the estimated value as obtained of the failure-state collection efficiency will have high accuracy.

In the exemplary aspect, the collection efficiency estimating unit may include an exhaust flow rate calculating unit that calculates an exhaust flow rate, and estimates the failure-state collection efficiency based on the exhaust flow rate calculated by the exhaust flow rate calculating unit.

In this regard, the inventors of the present invention have expertise that collection efficiency depends on exhaust flow rate. Thus, the collection efficiency estimating unit estimates a failure-state collection efficiency based on an exhaust flow rate. In this way, the estimated value as obtained of the failure-state collection efficiency will have high accuracy.

In the exemplary aspect, the deposit ratio estimating unit may include an electrode temperature estimating unit that estimates the temperature of the electrodes, and estimates the PM deposit ratio which becomes lower as the temperature of the electrodes estimated by the electrode temperature estimating unit becomes higher.

In this regard, the inventors of the present invention have expertise that higher temperature of the electrodes of the PM sensor makes PM deposit ratio lower being influenced by thermal migration. Thus, the electrode temperature estimating unit estimates the temperature of the electrodes. Then, the deposit ratio estimating unit estimates a PM deposit ratio which becomes lower as the temperature of the electrodes becomes higher. In this way, the estimated temperature as obtained of the PM deposit ratio will have high accuracy.

In the exemplary aspect, the electrode temperature estimating unit may include a heater resistance measuring unit that measures a heater resistance that is an electric resistance of the heater, and estimates the temperature of the electrodes based on the heater resistance measured by the heater resistance measuring unit.

The inventors of the present invention have expertise that the electrodes have a temperature equivalent to a heater resistance. Thus, the heater resistance measuring unit measures a heater resistance, while the electrode temperature estimating unit estimates the temperature of the electrodes based on the heater resistance. In this way, the estimated value as obtained of the temperature of the electrodes will have high accuracy.

In the exemplary aspect, the electrode temperature estimating unit may include a heat exchange amount calculating unit that calculates a heat exchange amount that is an amount of heat exchanged between the electrodes and the exhaust gas, and estimates the temperature of the electrodes based on the heat exchange amount calculated by the heat exchange amount calculating unit and a heat capacity of the electrodes.

Thus, the heat exchange amount calculating unit calculates the amount of heat exchanged between the electrodes and the exhaust gas. Thus, an approximate amount of heat taken away from the electrodes by the exhaust gas can be estimated. Also, the temperature of electrodes depends on the amount of heat taken away from the electrodes (heat exchange amount) and the heat capacity of the electrodes. Accordingly, the electrode temperature estimating unit estimates the temperature of the electrodes based on the heat exchange amount and the heat capacity of the electrodes. In this way, the estimated value as obtained of the temperature of the electrodes will have high accuracy.

In the exemplary aspect, the deposit ratio estimating unit may estimate the PM deposit ratio which becomes lower as the exhaust flow rate becomes larger.

The inventors of the present invention have expertise that PM deposit ratio becomes lower as exhaust flow rate becomes larger. Thus, the deposit ratio estimating unit estimates the PM deposit ratio which becomes lower as the exhaust flow rate becomes larger. In this way, the estimated value as obtained of the PM deposit ratio will have high accuracy.

In the exemplary aspect, the deposit ratio estimating unit estimates the PM deposit ratio which becomes lower as an elapsed time is shorter, the elapsed time being a time elapsed after a completion of the burning and removal of the PM due to the heater.

Thus, the temperature of the electrodes becomes higher as the time passage is shorter from the completion of the burning and removal of the PM by the heater. The inventors of the present invention have expertise that, when the temperature of electrodes is high, PM deposit ratio is lowered being influenced by thermal migration as mentioned above. Thus, the deposit ratio estimating unit estimates the PM deposit ratio which becomes lower as the time passage is shorter. In this way, the estimated value as obtained of the PM deposit ratio will have high accuracy.

BRIEF DESCRIPTION OF THE DRAWINGS

In the accompanying drawings:

FIG. 1 is a schematic diagram illustrating a configuration of an engine system of a vehicle which is equipped with a failure detection apparatus for a particulate filter, according to an embodiment of the present invention;

FIG. 3 is a flow diagram illustrating a process of detecting a failure of a DPF, according to the embodiment;

FIG. 12 is a flow diagram illustrating a process of detecting a failure of the DPF, according to a modification of the embodiment.

DETAILED DESCRIPTION OF THE PREFERRED EMBODIMENTS

Figure 2A:
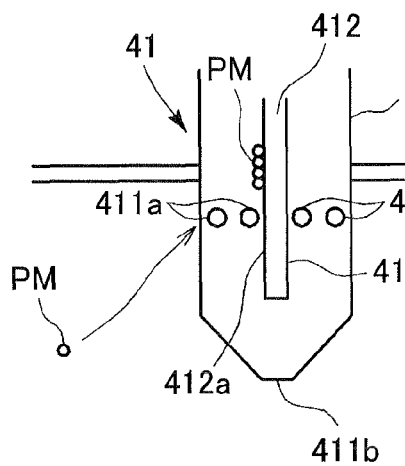
FIGS. 2A to 2E are diagrams illustrating a PM sensor included in the failure detection apparatus illustrated in FIG. 1.

With reference to the accompanying drawings, hereinafter is described a failure detection apparatus for a particulate filter according to an embodiment of the present invention.

FIG. 1 is a schematic diagram illustrating a configuration of an engine system 1 applied with the failure detection apparatus for a particulate filter according to the present embodiment. As shown in FIG. 1, the engine system 1 includes a diesel engine 10 (hereinafter referred to as "engine") as an internal combustion engine. The engine 10 includes an injector 11 that injects fuel into the combustion chamber. The engine 10 generates motive power by allowing the fuel injected from the injector 11 to ignite in the combustion chamber.

The engine 10 has an exhaust path 21 in which a diesel particulate filter (DPF) 30 is provided. The DPF 30 is a ceramic filter having a known configuration. For example, the DPF 30 is configured by forming a heat-resistant ceramic, such as cordierite, into a honeycomb structure in which a number of cells as gas passages are alternately closed at inlets side or outlets side. The exhaust gas emitted from the engine 10 flows downstream passing through porous partition walls of the DPF 30. In the course of the flow, particulate matter (PM) contained in the exhaust gas are collected and gradually accumulated. The PM constituting soot is composed of carbon particles.

The DPF 30 is not able to infinitely collect PM. Therefore, when the amount of PM accumulated (PM accumulation) in the DPF 30 is increased, regeneration treatment is performed to regenerate the DPM 30 by burning and removing the accumulated PM. For example, the regeneration process is performed by performing post injection once or by performing post injection in the form of multiple injection at a time point delayed by a predetermined time from the main fuel combustion (main injection) for obtaining motive power of the engine 10 (for generating output torque). Specifically, with the post injection, the temperature of the exhaust gas is elevated. At the same time, unburned fuel (hydrocarbon (HC)) is added to a diesel oxidation catalyst (DOC), not shown, provided upstream of the DPF 30 to burn PM using the reaction heat.

The temperature of the DPF 30 may be excessively elevated due to the regeneration process of the DPF 30. Specifically, when the state of regeneration process has turned to an idling state, the heat generated with the combustion of PM will stay in the DPF 30 because intake air is reduced in the idling state. As a result, the temperature of the DPF 30 may be excessively elevated. The excessively elevated temperature is likely to melt the DPF 30. Also, temperature difference in the DPF 30 is likely to cause thermal stress which in turn may break the DPF 30 (may cause a failure of the DPF 30). When the DPF 30 is in a failure state, the performance of collecting PM will be deteriorated. As a result, the amount of PM emitted outside the vehicle will be increased. In this regard, in the engine system 1 of the present embodiment, the DPF 30 is regarded as having a failure when the amount of PM emitted outside the vehicle has become equal to or more than a predetermined amount. Thus, the failure of the DPF 30 is detected. A specific process of detecting the failure will be described later.

The exhaust path 21 is provided with a PM sensor 41 at a downstream side 21*a* of the exhaust path 21 with respect to the DPF 30.

FIGS. 2A to 2E are diagrams illustrating the structure, function and the like of the PM sensor 41. FIG. 2A is an enlarged diagram of an area A in the vicinity of the PM sensor 41 illustrated in FIG. 1. As shown in FIG. 2A, the PM sensor 41 includes a casing 411 and a base 412. The base 412 provided in the casing 411 is transparently shown through the casing 411. Also, FIG. 2A illustrates the base 412 as viewed sideways.

As shown in FIG. 2A, the casing 411, which is hollow, of the PM sensor 41 is provide being exposed in the exhaust path 21*a*. The casing 411 is formed with a plurality of holes 411*a* that allow communication between the interior and the exterior of the casing 411. It is ensured that a part of the exhaust gas can enter the casing 411 through the holes 411*a*. The casing 411 is also formed with a discharge hole 411*b* through which the exhaust gas that has entered the casing 411 is discharged. The casing 411 shown in FIG. 2A has the discharge hole 411*b* at a tip end of the casing 411.

Figure 2B:
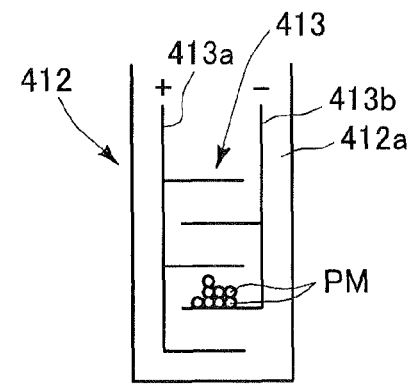

The base 412 is provided in the casing 411. The base 412 is made of an insulating material such as alumina. FIG. 2B illustrates the base 412 as viewed from the side of one base surface 412*a* (hereinafter referred to as "front surface 412*a*") (i.e. as viewed from the left in FIG. 2A). As shown in FIG. 2B, a pair of electrodes 413 (electrodes 413*a* and 413*b*) are provided on the front surface 412*a* of the base 412, being separated from and opposed to each other. A predetermined voltage is applied across the electrodes 413*a* and 413*b*. A part of PM contained in the exhaust gas that has entered the casing 411 is deposited on the front surface 412*a* of the base 412 (precisely, the surface 412*a* between the electrodes 413*a* and 413*b*). The PM that has not deposited on the base 412 is discharged from the discharge hole 411*b* formed in the casing 411.

Figure 2C:
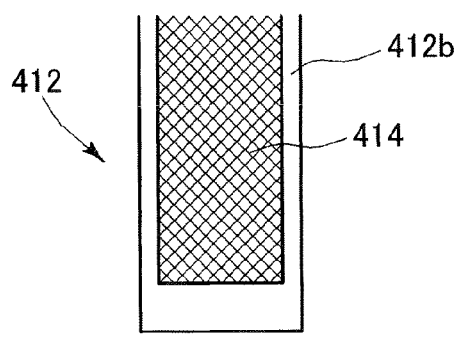

FIG. 2C illustrates the base 412 as viewed from the side of the other base surface 412*b* (hereinafter referred to as "rear surface 412*b*") (i.e. as viewed from the right in FIG. 2A). As shown in FIG. 2C, a heater 414 formed of a heating wire, which is made such as of platinum, for heating the base 412 is provided on the rear surface 412*b* of the base 412. The heater 414 heats the base 412 to burn and remove the PM deposited on the front surface 412*a* between the electrodes 413*a* and 413*b* provided on the base 412. Thus, the amount of PM is ensured to be repeatedly detected by the PM sensor 41.

Figure 2D:
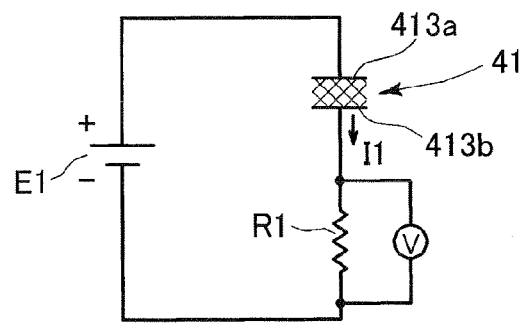
Figure 2E:
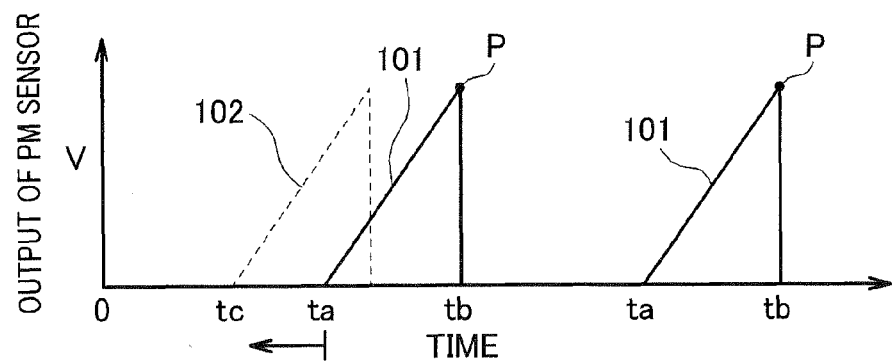

FIG. 2D illustrates a measurement circuit for measuring an output signal of the PM sensor 41. FIG. 2E illustrates an output signal of the PM sensor 41. Specifically, FIG. 2E shows a first line 101 and a second line 102 which indicate time variation of an output signal V of the PM sensor 41. The first line 101 indicates a normal state of the DPF 30, while the second line 102 indicates a failure state of the DPF 30. As shown in FIG. 2D, the measurement circuit is provided with a voltage source E1 to apply a predetermined voltage across the pair of electrodes 413*a* and 413*b* of the PM sensor 41.

As mentioned above, the base 412 is made of an insulating material and the two electrodes 413*a* and 413*b* are separated from each other. Accordingly, the electrodes 413*a* and 413*b* are insulated from each other in the state where no PM is deposited on the front surface 412*a*. In other words, no current I1 passes across the electrodes 413*a* and 413*b*.

When PM is deposited on the front surface 412*a* between the two electrodes 413*a* and 413*b*, and as far as the deposition is small, no current I1 will pass across the electrodes 413*a* and 413*b*. However, when PM of not less than a predetermined amount is deposited with time, current I1 will flow through the PM deposited between the two electrodes 413*a* and 413*b* because PM is composed of carbon particles having electrical conductivity. In other words, the measurement circuit is energized across the two electrodes 413*a* and 413*b*.

As shown in FIG. 2D, the measurement circuit is provided with a current-detecting resistor R1 (shunt resistor) on the line through which current I1 flows. Measuring the voltage across the shunt resistor R1, an output signal V equivalent to the current I1 is obtained.

In FIG. 2E, time t=0 indicates the time when PM starts depositing on the base 412. Soon after the time t=0, the output signal V is at a level of zero. As described above, this is because PM deposit amount is still small and thus the electrodes 413*a* and 413*b* are not electrically connected. With time t, PM deposit amount is increased and when time t passes a certain point, the output signal V starts appearing. This certain time point is regarded to be an energization timing. In FIG. 2E, the energization timing in a normal state of the DPF 30 is indicated by ta, while the energization timing in a failure state of the DPF 30 is indicated by tc.

The description hereinafter is give with reference to the line 101 in a normal state. After the energization timing ta, PM deposit amount is increased with time. Accordingly, the current I1, i.e. the level of the output signal V becomes higher. The output signal V will have a value equivalent to the PM deposit amount of the PM deposited on the base 412. The PM deposit amount has a value equivalent to the amount of PM (PM amount) contained in the exhaust gas. Therefore, the PM amount contained in the exhaust gas can be detected by reading the value of the output signal V. However, as described above, the electrical resistance of the PM deposited on the base 412 varies, to a great extent, depending on temperature. Therefore, it is difficult to detect a correct value of a PM amount from the absolute value of the output signal V.

When the PM detected at the time of the previous detection of PM deposition are left as they are on the base 412, the PM amount cannot be accurately detected this time. In this regard, the PM sensor 41 is adapted to periodically burn and remove the PM deposited on the base 412 by having the heater 414 (see FIG. 2C) heat the base 412. The heater 414 heats the base 412 at a temperature of about 700° C., for example, to burn and remove the PM. In this case, when the PM is burned and removed at a time point tb corresponding to a point P indicated in FIG. 2E, the level of the output signal V is reset to zero at the time point tb. After that, the PM again starts to deposit on the base 412 and the output signal V again starts appearing from the energization timing ta with reference to the time point tb.

The larger the amount of PM contained in the exhaust gas, the larger the amount of deposition on the base 412, and then the earlier PM sensor 41 is energized. When the DPF 30 is in a failure state, the amount of PM passing through the DPF 30 is increased compared to the normal state of the DPF 30. Accordingly, as shown in FIG. 2E, when the DPF 30 is in a failure state, energization timing tc comes earlier than the energization timing ta when the DPF 30 is in a normal state.

Referring again to FIG. 1, the engine system 1 includes a differential pressure sensor 42 that detects a differential pressure between the front and the rear of the DPF 30. The differential pressure sensor 42 has one end connected to the exhaust path 21 at an upstream side of the DPF 30 and the other end connected to the exhaust path 21 at a downstream side of the DPF 30. Also, the exhaust path 21 is provided with an exhaust temperature sensor 43 on an upstream side of the DPF 30 to detect the temperature of the exhaust gas.

The engine system 1 includes an intake path 52 which is provided with an airflow meter 44 that detects the amount of new air, and a throttle valve 45 (intake throttle valve) that regulates the amount of new air taken into the engine 10. The engine system 1 also includes an engine speed sensor 46 that detects the number of revolutions of the engine 10. For example, the engine speed sensor 46 may be a crank angle sensor that measures a rotation angle of a crank 12 which is coupled to the engine 10. The engine system 1 further includes an accelerator sensor 47 that detects the state (displacement) of the accelerator pedal. The accelerator sensor 47 corresponds to an operation unit that notifies a torque requested by the driver to the vehicle side.

The signals from the sensors 41 to 47 are ensured to be transmitted to an ECU 60 which will be described later.

The engine system 1 also includes an EGR (exhaust gas recirculation) system 50 that reduces generation of NOx by recirculating a part of the exhaust gas in an intake system and thereby reducing combustion temperature.

The engine system 1 includes an electronic control unit (ECU) 60 that controls the entire engine system 1. The ECU 60 is mainly configured to have a structure of a normally used computer, such as a microcontroller. The ECU 60 includes a central processing unit (CPU), not shown, that carries out various calculations, and a memory 61 (e.g., a read only memory (ROM) and random access memory (RAM)) that store various control programs and various pieces of information.

For example, the ECU 60 detects operating conditions based on the detection signals derived from the various sensors mentioned above. Then, the ECU 60 calculates optimal fuel injection quantity, injection timing and injection pressure and the like suitable for the operating conditions to thereby control fuel to be injected to the engine 10. Also, for example, the ECU 60 executes a control program prestored in the memory 61 (e.g., ROM) to perform the process of detecting a failure of the EPF 30. The process of detecting the failure (failure detection process) is specifically described below.

FIG. 3 is a flow diagram illustrating the failure detection process for the DPF 30, which is performed by the ECU 60. The process indicated in the flow diagram of FIG. 3 is performed by the ECU 60 by executing the control program stored in the memory 61 (e.g., ROM).

Figure 13:
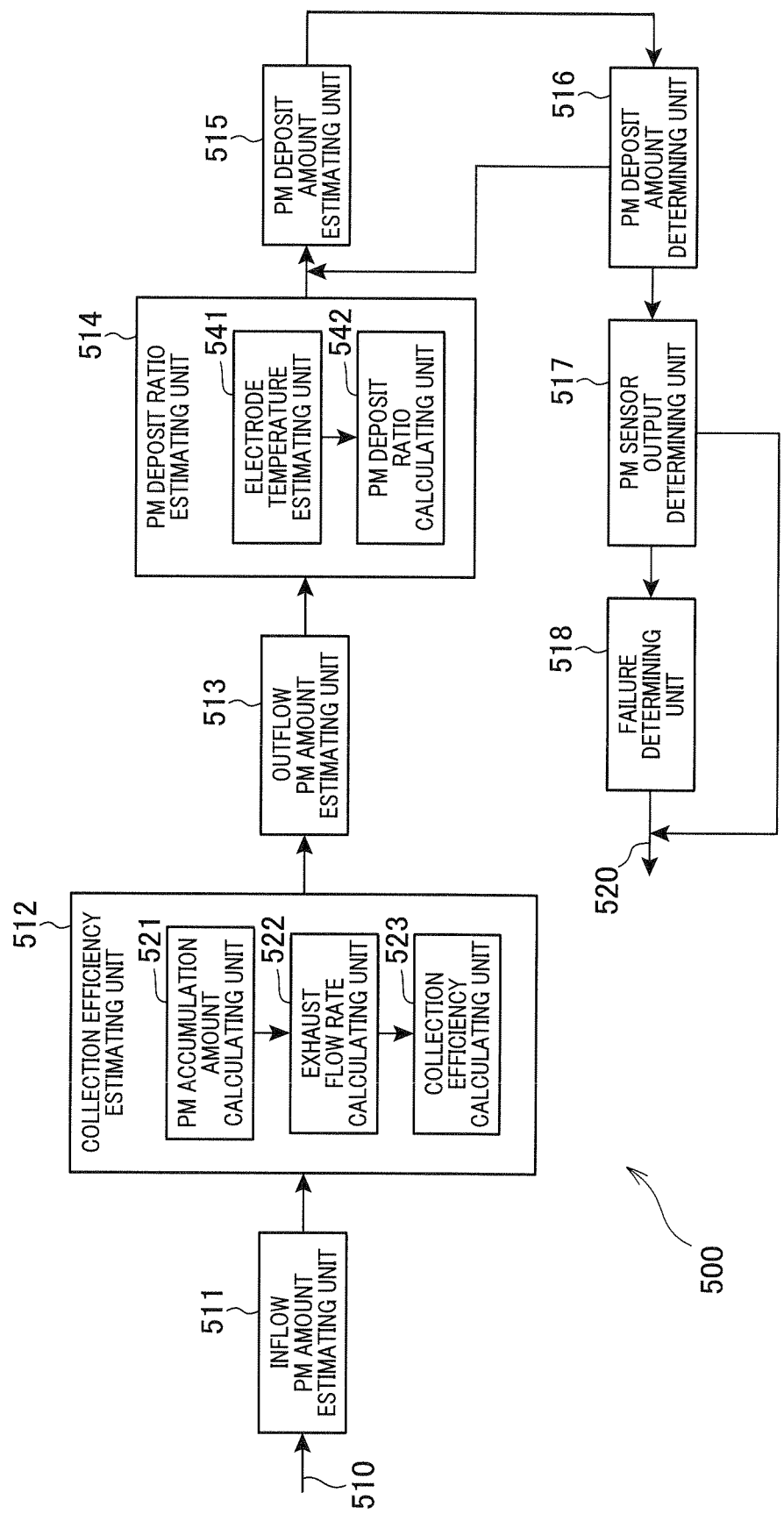
FIG. 13 is a schematic diagram illustrating a functional configuration of an ECU 60, which corresponds to the process shown in the flow diagram of FIG. 3.

FIG. 13 is a schematic diagram illustrating a functional configuration of the ECU 60, which corresponds to the failure detection process of the flow diagram illustrated in FIG. 3. As shown in FIG. 13, the ECU 60 includes a failure detection processor 500 that executes the control program prestored in the memory 61 (e.g., ROM) to detect a failure of the DPF 30. The failure detection processor 500 includes an inflow PM amount estimating unit 511, collection efficiency estimating section 512 (including a PM accumulation amount calculating unit 521, exhaust flow rate calculating unit 522 and collection efficiency calculating unit 523), outflow PM amount estimating unit 513, PM deposit ratio estimating unit 514 (including an electrode temperature estimating unit 541 and PM deposit ratio calculating unit 542), PM deposit amount estimating unit 515, PM deposit amount determining unit 516, PM sensor output determining unit 517 and failure determining unit 518.

The process shown in FIG. 3 is started by the ECU 60 immediately after the heater 414 (see FIG. 2C) of the PM sensor 41 has completed burning and removal of PM (at time point tb of FIG. 2E). As can be seen from the example shown in FIG. 13, in starting the process, a signal 510 is inputted to the failure detection processor 500 of the ECU 60 to control the starting timing (time point tb of FIG. 2E).

First, the ECU 60 estimates an inflow PM amount that is an amount of PM that has flowed into the DPF 30 (step S11). In the example of FIG. 13, this step is performed by the inflow PM amount estimating unit 511. The inflow PM amount is equivalent to the amount of PM exhausted from the engine 10. The amount of PM correlates to the engine speed of the engine 10 and fuel injection quantity.

Thus, at step S11, the ECU 60 estimates an inflow PM amount based such as on the engine speed of the engine 10 and fuel injection quantity. Specifically, a map of inflow PM amount is prestored in the memory 61 using the engine speed of the engine 10 and fuel injection quantity as parameters. The ECU 60 reads from the map an inflow PM amount correlating to the engine speed detected this time by the engine speed sensor 46 (see FIG. 1) and the command value of the quantity of fuel injected by the injector 11 (see FIG. 1).

Then, the ECU 60 estimates a failure-state collection efficiency that is a PM collection efficiency of the DPF 30 in a failure state (step S12). In the example of FIG. 13, this step is performed by the collection efficiency estimating unit 512. The expression "the DPF 30 in a failure state" here specifically refers to a state where the collection efficiency of the DPF 30 has drastically lowered due to the failure and thus the emission limits of OBD (On-Board-Diagnostics) cannot be satisfied. The emission limits of OBD are set to be stricter than that of e.g., Euro 6 standard. For example, in a specific driving mode, PM=4.5 mg/km is set according to the emission limits of Euro 6 standard, whereas PM=9.0 mg/kin, twice of the above, is set, for example, according to the emission limits of OBD.

Figure 4:
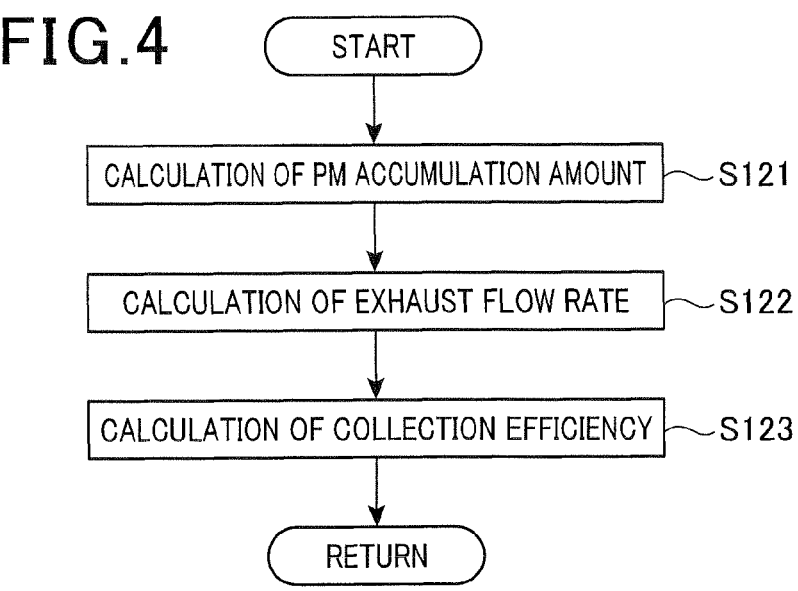
FIG. 4 is a flow diagram specifically illustrating a process of estimating a collection efficiency, which is performed at step S12 of the flow diagram illustrated in FIG. 3.

FIG. 4 is a flow diagram specifically illustrating the process performed at step S12. When the DPF 30 is in a failure state, the collection efficiency is lowered compared to that when the DPF 30 is in a normal state. In this regard, the inventors of the present invention have expertise that collection efficiency depends on a PM accumulation amount that is an amount of PM accumulated in the DPF30, and an exhaust flow rate.

Thus, the ECU 60 calculates first a PM accumulation amount that is an amount of PM accumulated in the DPF 30 (step S121). In the example of FIG. 13, this step is performed by the PM accumulation amount calculating unit 521. As the PM accumulation amount increases, the differential pressure between the front and the rear of the DPF 30 becomes larger. Accordingly, for example, the ECU 60 calculates, at step S121, a PM accumulation amount based on the differential pressure. Specifically, in the ECU 60, a map indicating correlation between differential pressure and PM accumulation amount is prestored in the memory 61. The ECU 60 reads from the map a PM accumulation amount correlating to the differential pressure detected this time by the differential sensor 42 (see FIG. 1).

Then, the ECU 60 calculates an exhaust flow rate (step S122). In the example of FIG. 13, this step is performed by the exhaust flow rate calculating unit 522. It should be appreciated that, at step S122, a volume flow rate is calculated as an exhaust flow rate.

Specifically, for example, the ECU 60 calculates an intake volume using the airflow meter 44. Then, the ECU 60 calculates an exhaust flow rate by correcting the intake volume using an expansion component and a compression component of the exhaust gas. The expansion component corresponds to the temperature of the exhaust gas detected by the exhaust temperature sensor 43, and the compression component corresponds to the pressure detected by a pressure sensor, not shown.

Figure 5A:
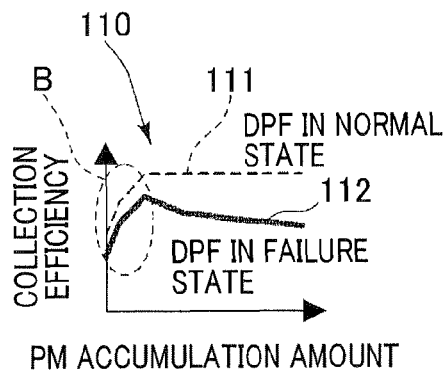
FIG. 5A is a diagram illustrating a correlation between PM accumulation amount in a DPF and collection efficiency of PM in the DPF, according to the embodiment.
Figure 5B:
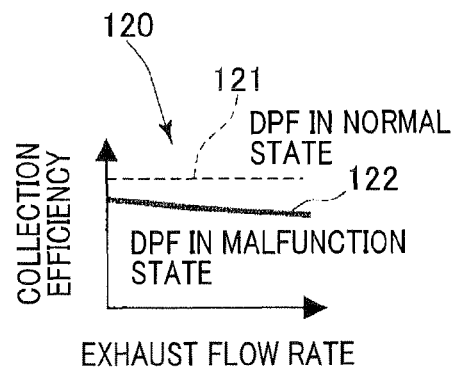
FIG. 5B is a diagram illustrating a correlation between exhaust flow rate and collection efficiency of PM in the DPF, according to the embodiment.

Then, the ECU 60 calculates the failure-state collection efficiency based on the PM accumulation amount and the exhaust flow rate (step S123). In the example of FIG. 13, this step is performed by the collection efficiency calculating unit 523. FIGS. 5A and 5B are diagrams illustrating correlations between PM accumulation amount and collection efficiency, and between exhaust flow rate and collection efficiency, respectively.

Specifically, FIG. 5A illustrates a graph 110 showing a correlation between PM accumulation amount and collection efficiency. The graph 110 shows a line 111 and a line 112. The line 111 indicates a correlation between PM accumulation amount and collection efficiency when the DPF 30 is in a normal state. The line 112 indicates a correlation between PM accumulation amount and collection efficiency when the DPF 30 is in a failure state. FIG. 5B illustrates a graph 120 showing a correlation between exhaust flow rate and collection efficiency. The graph 120 shows a line 121 and a line 122. The line 121 indicates a correlation between exhaust flow rate and collection efficiency when the DPF 30 is in a normal state. The line 122 indicates a correlation between exhaust flow rate and collection efficiency when the DPF 30 is in a failure state.

As indicated by the line 111 in FIG. 5A, in a normal state, collection efficiency is not so high in an area B where PM accumulation amount is small. However, as the PM accumulation amount increases, collection efficiency tends to be increased. Out of the area B, collection efficiency is maintained at a high level (e.g., 99% or more) irrespective of the PM accumulation amount.

On the other hand, as indicated by the line 112, in a failure state, collection efficiency is entirely lowered compared to the collection efficiency in a normal state. More specifically, in the area B where PM accumulation amount is small, collection efficiency is similar to that in a normal state. Out of the area B, however, collection efficiency tends to lower as PM accumulation amount increases. It is considered that this is because the pressure loss in a portion where PM is accumulated in the DPF 30 becomes higher as PM accumulation amount is increased and thus because more PM is permitted to pass through a broken portion of the DPF 30 where pressure loss is relatively small.

As mentioned above, collection efficiency tends to be low in the area B in both of normal and failure states. This tendency is based on the nature of PM, the nature being that the PM collected by the DPF 30 further collects different PM. In other words, it is considered that, when PM accumulation amount is small, the collected PM is unlikely to collect different PM and thus the collection efficiency is lowered.

As indicated by the line 121 in FIG. 5B, in the correlation between exhaust flow rate and collection efficiency in a normal state, the collection efficiency is maintained at a high level (e.g., 99% or more), irrespective of the exhaust flow rate. On the other hand, as indicated by the line 122, in a failure state, the collection efficiency tends to be lowered as the exhaust flow rate increases. It is considered that this is because the increase in the exhaust flow rate causes increase in the amount of PM passing through a broken portion of the DPF 30. However, it is also considered that the influence of the exhaust flow rate depends on the type of a failure of the DPF 30.

At step S123, the ECU 60 calculates a failure-state collection efficiency based on the correlations as shown in FIGS. 5A and 5B. Specifically, the ECU 60 prestores a map in the memory 61. The map includes correlations between PM accumulation amount and collection efficiency and between exhaust flow rate and collection efficiency in which the lines 112 and 122 of failure state as shown in FIGS. 5A and 5B are reflected. Then, the ECU 60 reads from the map a collection efficiency correlating to the PM accumulation amount calculated at step S121 and the exhaust flow are calculated at step S122. After completing step S123, the process shown in the flow diagram of FIG. 4 is ended and then control returns to the process shown in the flow diagram of FIG. 3.

As shown in FIG. 3, the ECU 60 estimates subsequently a failure-state outflow PM amount that is an amount of PM flowed out from the DPF 30 (passed through the DPF 30) in a failure state (step S13). In the example of FIG. 13, this step is performed by the outflow PM amount estimating unit 513. Specifically, the ECU 60 multiplies the inflow PM amount estimated at step S11 with the failure-state collection efficiency estimated at step S12 to thereby estimate a failure-state outflow PM amount.

Subsequently, the ECU 60 estimates a PM deposit ratio. The PM deposit ratio indicates a ratio of PM deposited on the base 412 (electrodes 413) of the PM sensor 41 among all of the PM contained in the exhaust gas at a downstream side of the DPF 30 (step S14). In the example of FIG. 13, this step is performed by the PM deposit ratio estimating unit 514.

Figure 6:
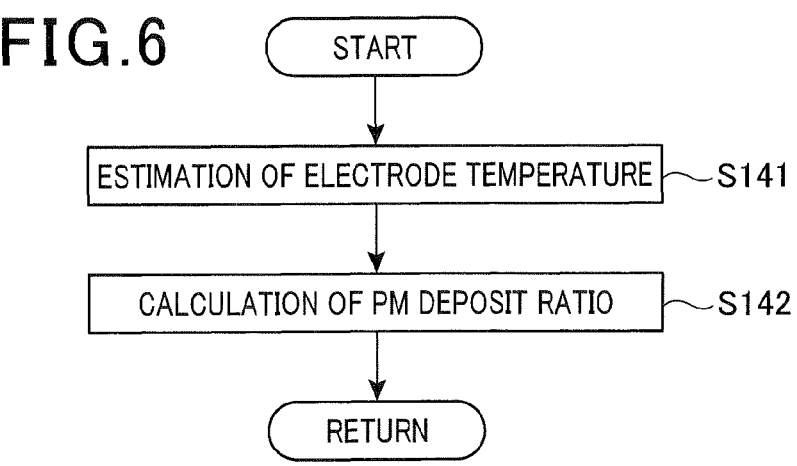
FIG. 6 is a flow diagram specifically illustrating a process of estimating a PM deposit amount, which is performed at step S14 of the flow diagram illustrated in FIG. 3.
Figure 7A:
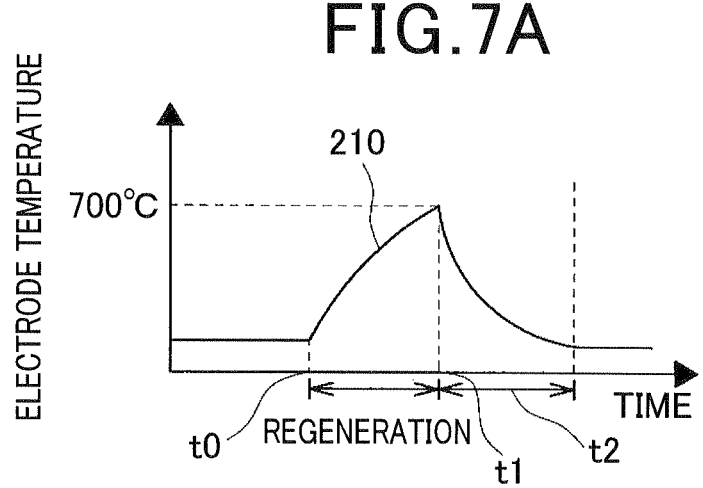
FIG. 7A is a diagram illustrating time variation of electrode temperature in the PM sensor.
Figure 7B:
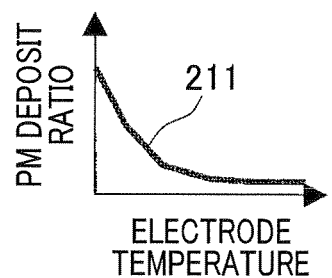
FIG. 7B is a diagram illustrating a correlation between electrode temperature and PM deposit ratio in the PM sensor.

FIG. 6 is a flow diagram specifically illustrating the process performed at step S14. FIGS. 7A and 7B are diagrams illustrating a correlation between the temperature of the electrodes 413 (electrode temperature) and PM deposit ratio. Specifically, FIG. 7A shows a line 210 that indicates how electrode temperature varies with time. FIG. 7B shows a line 211 that indicates a correlation between electrode temperature and PM deposit ratio.

Referring to FIGS. 7A and 7B, hereinafter is described the process of estimating PM deposit ratio performed at step S14.

As described above, when PM deposit amount is increased on the PM sensor 41, the base 412 (electrodes 413) is heated by the heater 414 (see FIG. 2C) to burn and remove the deposited PM. When the heating is started at time t=t0, the electrode temperature gradually increases, as shown in FIG. 7A, from the time t0.

Then, the heating (regeneration of the PM sensor 41) is finished at a temperature of about 700° C. that is the temperature at which the PM is burned and removed. When the heating is finished at time t=t1, the electrode temperature gradually decreases from the time t1. After the elapse of a predetermined time t2 from the time t1, the electrode temperature returns to the initial temperature that is the temperature before the base 412 is heated.

The failure detection process illustrated in FIG. 3 is started immediately after (t=t1 in FIG. 7A) regeneration of the PM sensor 41 is finished. Accordingly, while the failure detection process is performed, the electrode temperature drastically varies between 700° C. and the initial temperature. In this regard, as indicated by the line 211 in FIG. 7B, PM deposit ratio tends to be lowered as the electrode temperature is increased. This may be because high electrode temperature intensifies the influence of thermal migration. Thermal migration is caused by the difference between the electrode temperature and the temperature of the gas entered the casing 411 (electrode temperature>gas temperature).

As described above, PM deposit ratio depends on electrode temperature. Accordingly, the ECU 60 estimates, first, the electrode temperature of the present moment in order to estimate a PM deposit ratio (step S141). In the example of FIG. 13, this step is performed by the electrode temperature estimating unit 514.

Figure 8A:
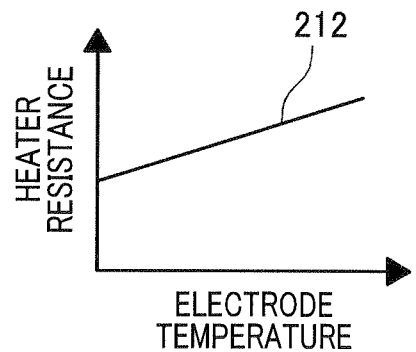
FIGS. 8A and 8B are diagrams illustrating a process of estimating an electrode temperature of the PM sensor, according to the embodiment.
Figure 8B:
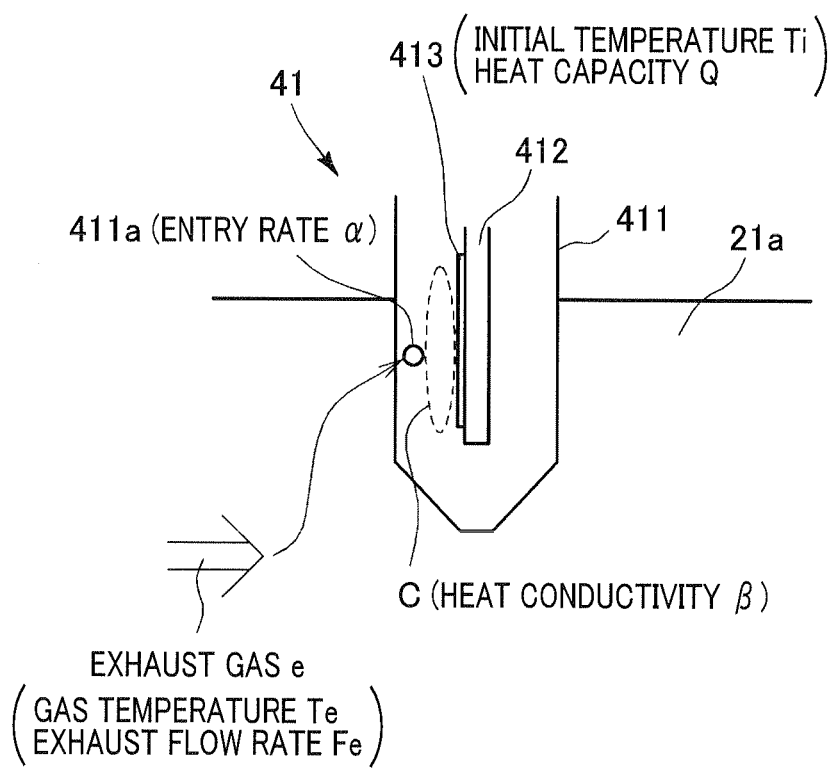

FIGS. 8A and 8B are diagrams illustrating the process of estimating electrode temperature. Specifically, FIG. 8A shows a line 212 that indicates a correlation between heater resistance and electrode temperature to explain the process of estimating electrode temperature based on the heater resistance of the heater 141. FIG. 8B is an enlarged view illustrating the vicinity of the PM sensor 41 to explain the process of estimating electrode temperature, taking into account the heat exchange between the electrodes 413 and the exhaust gas.

Referring to FIGS. 8A and 8B, the process of estimating electrode temperature is described.

First, hereinafter is described the process of estimating electrode temperature based on heater resistance.

The heater 414, when current passes therethrough, generates heat to heat the electrodes 413. In other words, the electrode temperature correlates to the amount of heat generated (hereinafter referred to as "heat generation rate") by the heater 414. As the heat generation rate of the heater 414 increases, the molecules composing the heater 414 are actively vibrated to increase the heat resistance.

Thus, as indicated by the line 212 in FIG. 8A, larger heat resistance makes larger the heat generation rate of the heater 414. As a result, the electrode temperature may be increased. When the heater 414 is made of platinum (Pt), substantially a linear (proportional) correlation is established between the heat resistance and the electrode temperature.

Thus, at step S141, the heater resistance is measured.

Figure 9:
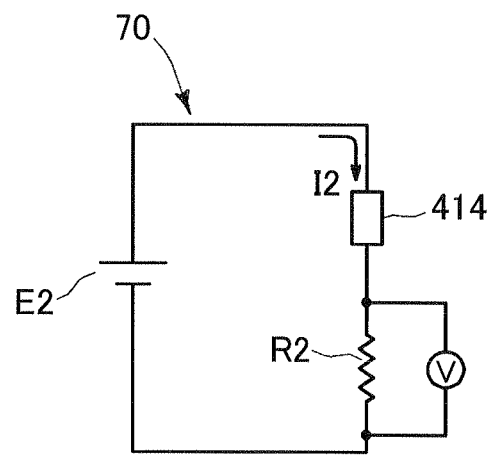
FIG. 9 is a diagram illustrating a measurement circuit that measures a heater resistance in the PM sensor.

FIG. 9 illustrates a measurement circuit 70 that measures the heater resistance. The measurement circuit 70 includes a voltage source E2 that applies voltage to the heater 414. When voltage is applied to the heater 414 by the voltage source E2, current I2 equivalent to the heater resistance passes through the heater 414. The measurement circuit 70 also includes a current-detecting resistor R2 (shunt resistor) on a line through which the current I2 flows. A voltage V across the shunt resistor R2 is measured to measure the current I2, i.e. the heater resistance.

In the ECU 60, a map including the line 212 of FIG. 8A is prestored in the memory 61. At step S141, the ECU 60 reads from the map an electrode temperature correlating to the heater resistance measured by the measurement circuit 70.

Hereinafter is described the process of estimating electrode temperature, taking into account the heat exchange between the electrodes 413 and the exhaust gas.

As shown in FIG. 8B, let us assume a model in which an exhaust gas e having a temperature Te (e.g., 100° C.) and a flow rate Fe flows through an exhaust path 21a. A portion of the exhaust gas e enters the casing 411 of the PM sensor 41 through the holes 411a formed in the casing 411. The rate that a portion of the exhaust gas e (portion of PM) enters the casing 411 is expressed as an entry rate α. Also, an initial temperature of the electrodes 413 is expressed by Ti (e.g., 700° C.) and a heat capacity is expressed by Q. Further, heat conductivity in the casing 411 (area C of FIG. 8B) is expressed as heat conductivity β.

In the above model, heat is exchanged between the high-temperature side electrodes 413 and the low-temperature side exhaust gas e. In this case, the temperature of the electrodes 413 will have a value equivalent to the amount of heat exchange (hereinafter referred to as "heat exchange rate") of the electrodes 413 and the heat capacity Q of the electrodes 413 (+base 412). For example, as the heat exchange rate is increased, the electrode temperature will be decreased. Further, as the heat capacity Q is increased, the temperature is more unlikely to be decreased with respect to the heat that has been taken away, and thus the electrode temperature will be increased.

Thus, at step S141, the ECU 60 calculates, first, a heat exchange rate X based on the various parameters (Te, Fe, α, Ti and β) mentioned above. Specifically, a map correlating the parameters (Te, Fe, α, Ti and β) with the heat exchange rate X is prestored in the memory 61 of the ECU 60. Then, the ECU 60 calculates the heat exchange rate X corresponding to the parameters (Te, Fe, α, Ti and β) this time based on the map. In this case, the exhaust temperature Te is detected by the exhaust temperature sensor 43 (see FIG. 1). As the exhaust flow rate Fe, the value calculated at step S122 mentioned above is used. The entry rate α is pre-determined, taking into account of the shape or the like of the holes 411a. As the initial temperature Ti of the electrodes 413, a predetermined value (e.g., 700° C.) is used. Also, as the heat conductivity β, a predetermined value (e.g., heat conductivity of air) is used. Since heat exchange models between two materials are well known, further specific description of such models is omitted.

After calculating the heat exchange rate X, the ECU 60 calculates an electrode temperature based on the heat exchange rate X and the heat capacity Q of the electrodes 413. Specifically, a map correlating the heat exchange rate X and the heat capacity Q with electrode temperature is prestored in the memory 61 of the ECU 60. Thus, the ECU 60 calculates an electrode temperature corresponding to the heat exchange rate X and the heat capacity Q this time based on the map. In this case, the heat capacity Q will have a value suitable for the area of the electrodes 413. Accordingly, as the heat capacity Q, a value calculated in advance based on the area is used.

After estimating an electrode temperature at step S141, the ECU 60 estimates a PM deposit ratio based on the electrode temperature (step S142). In the example of FIG. 13, this step is performed by the PM deposit ratio calculating unit 542. Specifically, the line 211 correlating the electrode temperature with PM deposit ratio as shown in FIG. 7B is prestored in the memory 61 of the ECU 60. Thus, the ECU 60 reads from the line 211 a PM deposit ratio correlating to the electrode temperature this time. After performing step S142, the process of the flow diagram illustrated in FIG. 6 is ended and then control returns to the process shown in the flow diagram of FIG. 3.

The process of estimating PM deposit ratio described above is based on electrode temperature. However, PM deposit ratio may be estimated through different processes. Hereinafter is described another process of estimating PM deposit ratio.

Figure 10A:
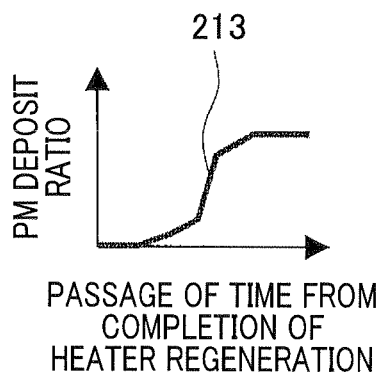
FIG. 10A is a diagram illustrating a correlation between passage of time from the completion of heater regeneration of the PM sensor and PM deposit ratio in the PM sensor.

As indicated in FIG. 7A by the line 210 of time variation of electrode temperature, electrode temperature gradually decreases with time after completion of heating at time t1 by the heater 411 (regeneration by the heater 414). In other words, the electrode temperature varies with time after completing regeneration by the heater 414. When electrode temperature varies, PM deposit ratio also varies (see FIG. 7B) and thus a PM deposit ratio can be directly estimated from an elapsed time. In this regard, FIG. 10A shows a line 213 which indicates a correlation between the elapsed time and PM deposit ratio. As indicated by the line 213, the shorter the elapsed time becomes, the lower the PM deposit ratio becomes. This is because, when the elapsed time becomes shorter, the electrode temperature becomes higher.

Thus, at step S14 of FIG. 3, the line 213 of FIG. 10A is prestored in the memory 61 of the ECU 60. Then, the ECU 60 may read from the line 213 a PM deposit ratio correlating to the elapsed time this time. It should be appreciated that the elapsed time may be measured such as by a timer, not shown, incorporated in the ECU 60. The process of estimating PM deposit ratio from passage of time is performed replacing the process shown in FIG. 6.

Figure 10B:
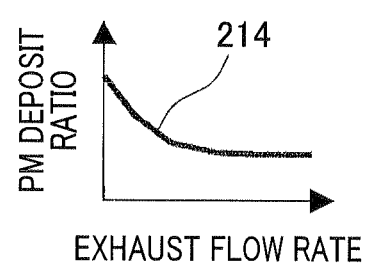
FIG. 10B is a diagram illustrating a correlation between exhaust flow rate and PM deposit ratio in the PM sensor.

A PM deposit ratio, besides being estimated from passage of time, may be estimated from exhaust flow rate. In this regard, FIG. 10B shows a line 214 which indicates a correlation between exhaust flow rate and PM deposit ratio. As indicated by the line 214, a higher exhaust flow rate makes lower the PM deposit ratio. This is because, when an exhaust flow rate is higher, the flow speed of the exhaust gas becomes higher.

Thus, at step S14, the line 214 of FIG. 10B is prestored in the memory 61 of the ECU 60. Then, the ECU 60 may read from the line 214 a PM deposit ratio correlating to the exhaust flow rate this time. It should be appreciated that the value calculated at step S122 described above is used as the exhaust flow rate. The process of estimating PM deposit ratio from exhaust flow rate is performed replacing or in addition to the process shown in FIG. 6. When a PM deposit ratio is estimated based on an exhaust flow rate in addition to the process shown in FIG. 6, or when a PM deposit ratio is estimated based on both of electrode temperature and exhaust flow rate, a map correlating PM deposit ratio with both of electrode temperature and exhaust flow rate may be prepared and prestored in the memory 61.

Referring again to FIG. 3, processing subsequent to step S14 is described. After step S14, the ECU 60 estimates an amount of PM deposited on the PM sensor 41 when the DPF 30 is in a failure state (failure-state PM deposit amount) (step S15). In the example shown in FIG. 13, this step is performed by the PM deposit amount estimating unit 515. Specifically, the ECU 60 multiplies the failure-state outflow PM amount estimated at step S13 with the PM deposit ratio estimated at step S14 to calculate a failure-state PM deposit amount.

Before describing step S16 onward, hereinafter is described a process of estimating a failure-state energization timing that is the energization timing when the DPF 30 is in a failure state.

Figure 11A:
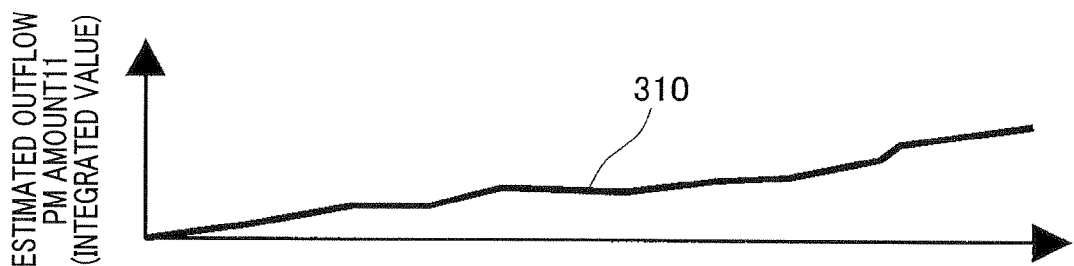
FIGS. 11A to 11C are diagrams illustrating a process of estimating failure-state energization timing of the PM sensor at the occurrence of a failure of the DPF and a process of determining the occurrence of a failure of the DPF based on the failure-state energization timing, according to the embodiment.
Figure 11B:
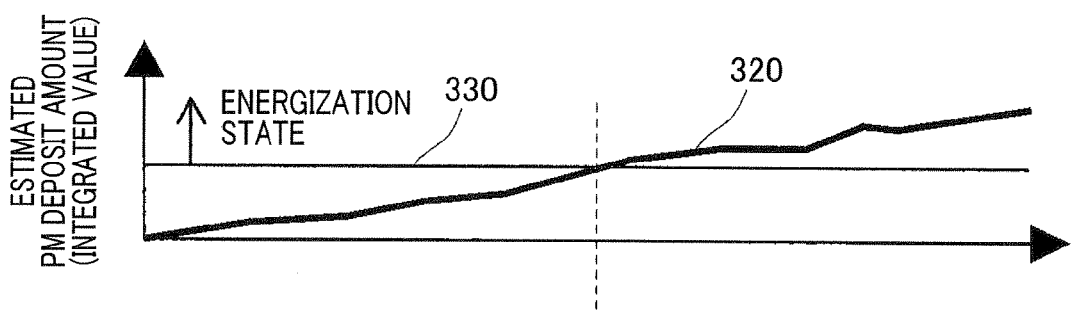
Figure 11C:
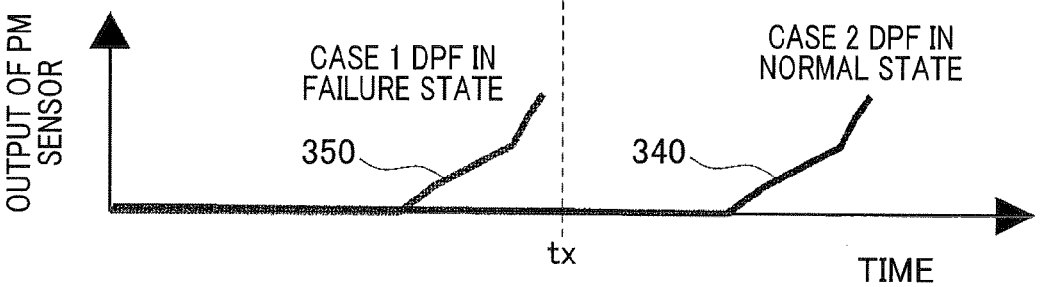

FIGS. 11A to 11C illustrate the process of the estimation. Specifically, FIG. 11A shows a line 310 which indicates time variation of an integrated value of the failure-state outflow PM amount estimated at step S13. FIG. 11B shows a line 320 which indicates time variation of an integrated value of the failure-state PM deposit amount estimated at step S15. In FIG. 11B, a line 330 indicates a predetermined energization deposition (hereinafter also just referred to as "energization deposition") as a PM deposit amount that allows the PM sensor 41 to start being energized. FIG. 11C shows lines (line 340 in a normal state and line 350 in a failure state) that indicate time variations of an output signal from the PM sensor 41. In FIGS. 11A to 11C, time t=0 indicates a time point immediately after completing burning and removal of PM by the heater 414, i.e. a time point when the process shown in FIG. 3 is started.

As shown in FIGS. 11A and 11B, the integrated value of the failure-state outflow PM amount is gradually increased with time (line 310). Accompanying this, the integrated value of the failure-state PM deposit amount is also gradually increased with time (line 320). As shown in FIG. 11B, when the DPF 30 is in a failure state, it will take some time before the integrated value of the failure-state PM deposit amount becomes equal to the energization deposit amount (before the line 320 crosses the line 330). Then, when the integrated value of the failure-state PM deposit amount has become equal to the energization deposit amount (when the line 320 has crossed the line 330), the PM sensor 41 becomes energized. This energization timing is rendered to be energization timing tx of the DPF 30 in a failure state (failure-state energization timing).

As described above, in the present embodiment, the occurrence of a failure in the DPF 30 is defined to be the case where the emission limits of OBD (On-Board-Diagnostics) are no longer satisfied. Thus, in the present embodiment, the failure-state energization timing tx in such a case is estimated. Also, in the present embodiment, the occurrence of a failure in the DPF 30 is determined based on whether the actual energization timing of the PM sensor 41 is before or after the failure-state energization timing tx.

Therefore, subsequent to the step S15 of FIG. 3, the ECU 60 determines whether or not the failure-state PM deposit amount estimated at step S15 has become equal to or more than the energization deposit amount with which the PM sensor 41 has become energized (step S16). In the example of FIG. 13, this step is performed by the PM deposit amount determining unit 516.

If the energization deposit amount has not been reached (No at step S16), control returns to step S15. At step S15, the ECU 60 calculates the subsequent failure-state PM deposit amount based on the results of the subsequently run steps S11 to S14. Then, the ECU 60 integrates the failure-state PM deposit amount with respect to the failure-state PM deposit amounts up to the previous time (step S16). In other words, as shown in FIG. 11B, before reaching the energization deposit amount, the calculated integrated value of the failure-state PM deposit amount gradually increases with time (step S15).

If the integrated value of the failure-state PM deposit amount has reached the energization deposition (Yes at step S16), the ECU 60 estimates the time point reached as being the failure-state energization timing (failure-state energization timing tx of FIGS. 11B and 11C) to recognize the actual presence/absence of the output of the PM sensor 41. Specifically, the ECU 60 determines whether the output of the PM sensor 41 is not less than a predetermined value to determine whether or not the PM sensor 41 is energized (step S17). In the example of FIG. 13, this step is performed by the PM sensor output determining unit 517. The predetermined value at step S17 is used for determining whether or not the PM sensor 41 is energized and thus is approximately set to zero on the vertical axis of FIG. 11C.

If the output of the PM sensor 41 is less than the predetermined value, or if the PM sensor 41 has not yet become energized (No at step S17), the process of the flow diagram illustrated in FIG. 3 is ended. In this case, the actual energization timing of the PM sensor 41 is later than the failure-state energization timing. Accordingly, the DPF 30 is determined to be in a normal state (see the line 340 of FIG. 11C). In this case, the DPF 30 satisfies the emission limits of OBD. In the example of FIG. 13, a signal 520 is outputted to indicate the results of failure determination, i.e. to indicate that the DPF 30 is in a normal state.

On the other hand, if the output of the PM sensor 41 is not less than the predetermined value, or if the PM sensor 41 has become energized (Yes at step S17), control proceeds to step S18. In this case, the actual energization timing of the PM sensor 41 is earlier than the failure-state energization timing. Accordingly, at step S18, the ECU 60 determines that the DPF 30 is in a failure state (step S18) (see the line 350 of FIG. 11C). In the example of FIG. 13, this step is performed by the failure determining unit 518. In this case, the DPF 30 is unlikely to satisfy the emission limits of OBD. In this case, in the example of FIG. 13, the signal 520 is outputted to indicate the results of failure determination, i.e. to indicate that the DPF 30 is in a failure state. Then, the process of the flow diagram illustrated in FIG. 3 is ended.

As described above, in the present embodiment, the occurrence of failure in the DPF 30 is determined based on the energization timing of the PM sensor 41. Accordingly, the failure of the DPF 30 can be detected with good accuracy, irrespective of the temperature variation of the PM deposited on the PM sensor 41. In this case, the energization timing (failure-state energization timing) when the DPF 30 is in a failure state is estimated based on various conditions, i.e. inflow PM amount, collection efficiency, outflow PM amount, PM deposit ratio and PM deposit amount (steps S11 to S15). Therefore, the estimated value as obtained of the failure-state energization timing will have high accuracy.

Modifications

Some modifications of the above embodiment will be described. In the modifications, the components or steps identical with or similar to those in the above embodiment are given the same reference numerals for the sake of omitting unnecessary explanation.

In the embodiment described above, the presence/absence of output of the PM sensor 41 is recognized after the failure-state energization timing has come (Yes at step S16 step S17 of FIG. 3). However, the failure-state energization timing may be recognized as having or not having come after the output of the PM sensor 41. In this case, the process of a flow diagram of FIG. 12, for example, may be performed replacing the process of FIG. 3. FIG. 12 is the flow diagram illustrating a failure detection process according to a modification.

The process shown in FIG. 12 is different from the process of FIG. 3 in that steps S11 to S15 are followed by step S17 which is then followed by step S16.

Specifically, after estimating a failure-state PM deposit amount at steps S11 to S15, the ECU 60 determines whether or not the output of the PM sensor 41 is not less than the predetermined value to recognize the presence/absence of the output of the PM sensor 41 (step S17). If the output of the PM sensor 41 is less than the predetermined value, or if the PM sensor 41 is yet to have an output (No at step S17), control returns to step S17 where the output of the PM sensor 41 is waited. If the output of the PM sensor 41 is not less than the predetermined value, or if the PM sensor 41 does have an output (Yes at step S17), control proceeds to step S16. In this case, the actual energization timing of the PM sensor 41 has come.

Subsequently, the ECU 60 determines whether or not the integrated value of the failure-state PM deposit amount is equal to or more than the energization deposition (step S16). If the integrated value of the failure-state PM deposit amount is equal to or more than the energization deposition (Yes at step S16), the process of the flow diagram illustrated in FIG. 12 is ended. In this case, the failure-state energization timing comes first and then the actual energization timing comes. Thus, the DPF 30 is determined to be in a normal state.

On the other hand, if the integrated value of the failure-state PM deposit amount has not reached the energization deposition (No at step S16), control proceeds to step S18. In this case, the actual energization timing comes earlier than the failure-state energization timing. Thus, the ECU 60 determines that the DPF 30 is in a failure state (step S18). Then, the process of the flow diagram illustrated in FIG. 12 is ended.

In the above embodiment, the ECU 60 that performs processes of steps S11-S16 in FIG. 3 or 12 (inflow PM amount estimating unit 511, collection efficiency estimating section 512, outflow PM amount estimating unit 513, PM deposit ratio estimating unit 514, PM deposit amount estimating unit 515, PM deposit amount determining unit 516 in FIG. 13) corresponds to a timing estimating unit. The ECU 60 that performs a process of step S18 in FIG. 3 or 12 (failure determining unit 518 in FIG. 13) corresponds to a failure determining unit. The ECU 60 that performs a process of step S11 in FIG. 3 or 12 (inflow PM amount estimating unit 511 in FIG. 13) corresponds to an inflow PM amount estimating unit. The ECU 60 that performs a process of step S12 in FIG. 3 or 12 (collection efficiency estimating unit 512 in FIG. 13) corresponds to a collection efficiency estimating unit. The ECU 60 that performs a process of step S13 in FIG. 3 or 12 (outflow PM amount estimating unit 513 in FIG. 13) corresponds to outflow PM amount estimating unit. The ECU 60 that performs a process of step S14 in FIG. 3 or 12 (PM deposit ratio estimating unit 514 in FIG. 13) corresponds to a deposit ratio estimating unit. The ECU 60 that performs a process of step S15 in FIG. 3 or 12 (PM deposit amount estimating unit in FIG. 13) corresponds to a deposit amount calculating unit. The ECU 60 that performs a process of step S121 in FIG. 4 (PM accumulation amount calculating unit 521 in FIG. 13) corresponds to an accumulation amount calculation unit. The ECU 60 that performs a process of step S122 in FIG. 4 (exhaust flow rate calculating unit 522 in FIG. 13) corresponds to an exhaust flow rate calculating unit. The ECU 60 that performs a process of step S141 in FIG. 6 (electrode temperature estimating unit 541 in FIG. 13) corresponds to an electrode temperature estimating unit and a heater resistance measuring unit. The measurement circuit 70 in FIG. 9 corresponds to a heater resistance measuring unit.

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A failure detection apparatus for a particulate filter, comprising:
    a particulate filter that is disposed in an exhaust passage of an internal combustion engine and collects particulate matter (PM) contained in exhaust gas;
    a PM sensor that is disposed at a downstream side of the particulate filter in the exhaust passage and detects an amount of the PM in contained in exhaust gas at the downstream side of the particulate filter, the PM sensor including an electrode and detecting amount of the PM based on current passing through the particulate matter deposited on the electrode;
    timing estimating means for estimating a failure-state energization timing that is an energization timing at which the PM sensor starts to be energized due to the particulate matter deposited on the electrode assuming that the particulate filter has failed; and
    failure determining means for determining that the particulate filter is in a failure state when an actual energization timing of the PM sensor is earlier than the failure-state energization timing.

2. The failure detection apparatus for the particulate filter according to claim 1, wherein:
    the PM sensor includes a heater that heats the PM sensor to burn and remove the PM deposited on the electrode; and the timing estimating means estimates the failure-state energization timing after a burning and removal of the PM due to the heater.

3. The failure detection device for the particulate filter according to claim 2, wherein:
the timing estimating means includes
inflow PM amount estimating means for estimating an inflow PM amount that is an amount of the PM flowing into the particulate filter,
collection efficiency estimating means for estimating a failure-state collection efficiency that is a collection efficiency of the particulate filter assuming that the particulate filter has failed, and
outflow PM amount estimating means for estimating a failure-state outflow PM amount that is an amount of the PM flowing out of the particulate filter assuming that the particulate filter has failed based on the inflow PM amount estimated by the inflow PM amount estimating means and the failure-state collection efficiency estimated by the collection efficiency estimating means; and
the timing estimating means estimates the failure-state energization timing based on the failure-state outflow PM amount estimated by the outflow PM amount estimating means.

4. The failure detection apparatus for the particulate filter according to claim 3, wherein:
the timing estimating means includes
deposit ratio estimating unit means for estimating a PM deposit ratio that is a ratio of the PM deposited on the electrode with respect to all of the PM included in exhaust gas at a downstream side of the particulate filter in the exhaust passage;
deposit amount calculating means for calculating an integrated value of a failure-state PM deposit amount by integrating the failure-state PM deposit amount with time, the failure-state PM deposit amount being an amount of the PM deposited the electrode assuming that the particulate filter has failed; and
the timing estimating means estimates, as the failure-state energization timing, an timing at which the integrated value of the failure-state PM deposit amount becomes not less than a energization deposit amount that is predetermined as an PM deposit amount at the energization timing.

5. The failure detection apparatus for the particulate filter according to claim 4, wherein:
the collection efficiency estimating means includes an accumulation amount calculation means for calculating a PM accumulation amount that is an amount of the PM accumulated on the particulate filter, and estimates the failure-state collection efficiency based on the PM accumulation amount by the accumulation calculation means.

6. The failure detection apparatus for the particulate filter according to claim 5, wherein:
the collection efficiency estimating means includes an exhaust flow rate calculating means for calculating an exhaust flow rate, and estimates the failure-state collection efficiency based on the exhaust flow rate calculated by the exhaust flow rate calculating means.

7. The failure detection apparatus for the particulate filter according to claim 3, wherein:
the collection efficiency estimating means includes an accumulation amount calculation means for calculating a PM accumulation amount that is an amount of the PM accumulated on the particulate filter, and estimates the failure-state collection efficiency based on the PM accumulation amount by the accumulation calculation means.

8. The failure detection apparatus for the particulate filter according to claim 7, wherein:
the collection efficiency estimating means includes an exhaust flow rate calculating means for calculating an exhaust flow rate, and estimates the failure-state collection efficiency based on the exhaust flow rate calculated by the exhaust flow rate calculating means.

9. The failure detection apparatus for the particulate filter according to claim 3, wherein:
the collection efficiency estimating means includes an exhaust flow rate calculating means for calculating an exhaust flow rate, and estimates the failure-state collection efficiency based on the exhaust flow rate calculated by the exhaust flow rate calculating means.

10. The failure detection apparatus for the particulate filter according to claim 4, wherein:
the collection efficiency estimating means includes an exhaust flow rate calculating means for calculating an exhaust flow rate, and estimates the failure-state collection efficiency based on the exhaust flow rate calculated by the exhaust flow rate calculating means.

11. The failure detection apparatus for the particulate filter according to claim 4, wherein:
the deposit ratio estimating means includes an electrode temperature estimating means for estimating the temperature of the electrodes, and estimates the PM deposit ratio which becomes lower as the temperature of the electrodes estimated by the electrode temperature estimating means becomes higher.

12. The failure detection apparatus for the particulate filter according to claim 11, further comprising:
heater resistance measuring means for measuring a heater resistance that is an electric resistance of the heater,
wherein the electrode temperature estimating means estimates the temperature of the electrodes based on the heater resistance measured by the heater resistance measuring means.

13. The failure detection apparatus for the particulate filter according to claim 11, wherein:
the electrode temperature estimating means includes a heat exchange amount calculating means for calculating a heat exchange amount that is an amount of heat exchanged between the electrode and the exhaust gas, and estimates the temperature of the electrodes based on the heat exchange amount calculated by the heat exchange amount calculating means and a heat capacity of the electrode.

14. The failure detection apparatus for the particulate filter according to claim 4, wherein:
the deposit ratio estimating means estimates the PM deposit ratio which becomes lower as the exhaust flow rate becomes larger.

15. The failure detection apparatus for the particulate filter according to claim 4, wherein:
the deposit ratio estimating means estimates the PM deposit ratio which becomes lower as an elapsed time is shorter, the elapsed time being a time elapsed after a completion of the burning and removal of the PM due to the heater.

* * * * *